United States Patent [19]

Gamba

[11] 4,063,089

[45] Dec. 13, 1977

[54] X-RAY CHEMICAL ANALYZER FOR FIELD APPLICATIONS

[75] Inventor: Otto O. M. Gamba, Clairton, Pa.

[73] Assignee: The United States of America as represented by the United States Energy Research and Development Administration, Washington, D.C.

[21] Appl. No.: 744,493

[22] Filed: Nov. 24, 1976

[51] Int. Cl.² .......................................... G01N 23/20
[52] U.S. Cl. ................................. 250/272; 250/308; 250/370
[58] Field of Search ............... 250/272, 273, 370, 308, 250/496

[56] References Cited

U.S. PATENT DOCUMENTS

| | | | |
|---|---|---|---|
| 3,319,065 | 5/1967 | Webster | 250/272 |
| 3,751,661 | 8/1973 | Packer et al. | 250/370 |
| 3,864,570 | 2/1975 | Zingaro | 250/370 |
| 3,889,113 | 6/1975 | Rhodes | 250/272 |

Primary Examiner—Harold A. Dixon
Attorney, Agent, or Firm—Dean E. Carlson

[57] ABSTRACT

A self-supporting portable field multichannel X-ray chemical analyzer system comprising a lightweight, flexibly connected, remotely locatable, radioisotope-excited sensing probe utilizing a cryogenically-cooled solid state semi-conductor crystal detector for fast in situ non-destructive, qualitative and quantitative analysis of elements in solid, powder, liquid or slurried form, utilizing an X-ray energy dispersive spectrometry technique.

3 Claims, 3 Drawing Figures

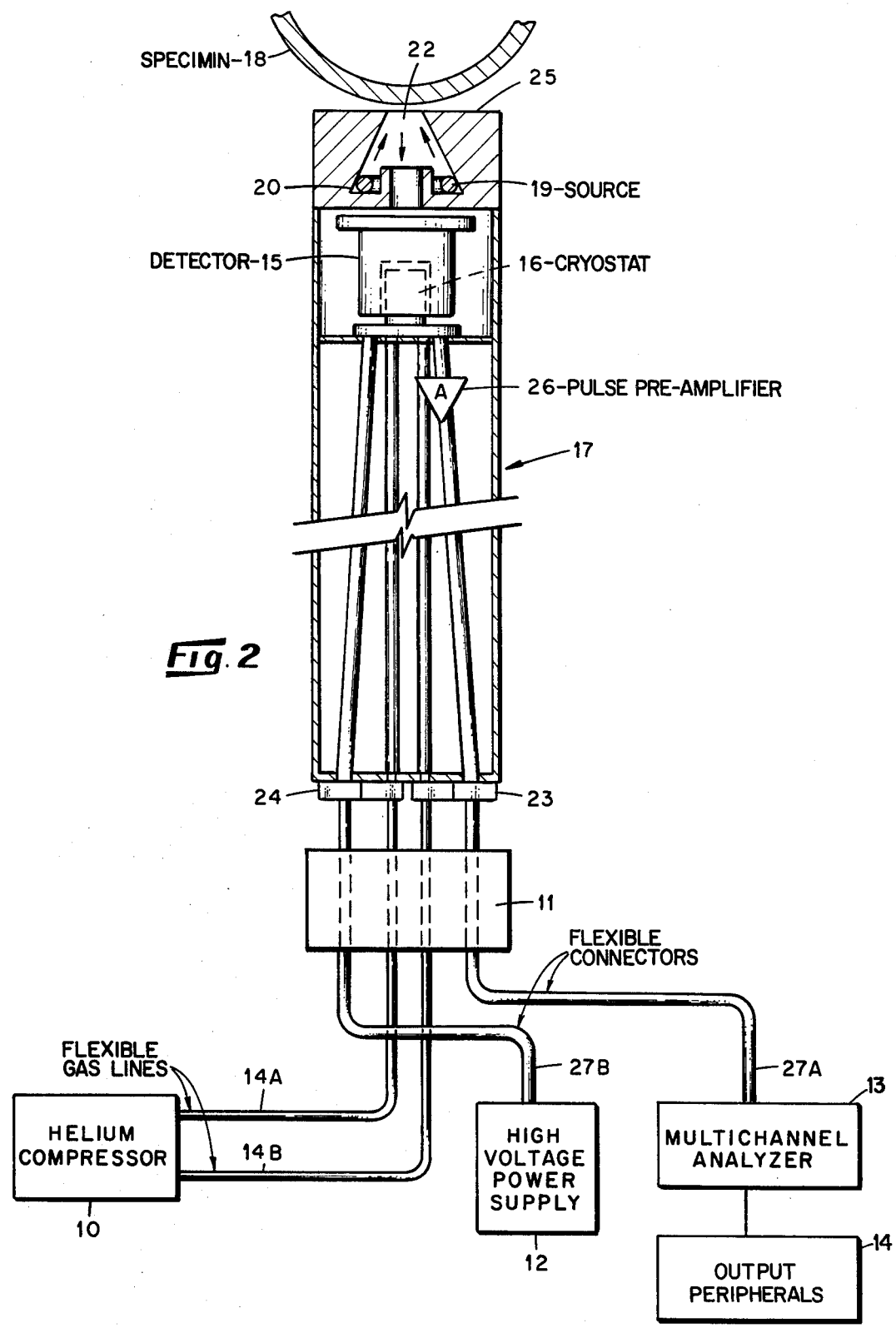

X-RAY CHEMICAL ANALYZER FOR FIELD APPLICATIONS

BACKGROUND OF THE INVENTION

It is well-known in the art that various excitation sources may be used to fluoresce the characteristic X-radiation of unknown elements that may be present in a sample specimen and thereby identify them. In accordance with this well-known energy dispersal spectrometry method, various kinds of detector systems are utilized to measure the energy level and intensity of the X-ray photons that are emitted from the sample, and which, identify the elements and indicate their concentration. Representative prior art systems are shown in U.S. Pat. Nos. 3,154,684, 3,621,245, and 3,196,272. However, the prior art does not address the problem of obtaining analytical results under commonly encountered field conditions where the specimen is obscured or remotely located, or where the parts cannot be sectioned or transported for analysis in the laboratory. Existing systems are designed primarily for laboratory and stationary use and their size and weight renders them nonportable and thereby inherently unsuitable for field use.

Accordingly, it is an object of this invention to provide a self-supporting, portable, chemical analyzer useful for on-the-spot analysis of unknown specimens under field conditions even where such specimens are obscured or located in remote locations. Another object of this invention to provide a system that is not dependent on consumable cryogenic fluids and is utilizable with streamlined analytical procedures without affecting the quality of the analysis. A further object of this invention is to provide a system capable of continuously monitoring specimens.

SUMMARY OF THE INVENTION

According to the present invention there is provided a self-supporting portable field multichannel chemical analyzing system. A radioisotope excitation source is used to fluoresce the characteristic X-radiation of the elements present in the sample. A solid state detector is utilized to measure with very high resolution the energy of the X-ray photons generated by the sample. The output pulse amplitude of the detector is directly proportional to the energy of the incident X-ray photon, and is used to identify the emitting element.

The pulses emitted from the detector are sorted by their energy level, recorded in the ferrite core memory of a multichannel X-ray analyzer, and displayed on a cathode ray tube, recorded on an X-Y plotter, or recorded by additional attachments such as a printer. The cryogenic temperature necessary for the operation of the solid state detector is supplied by a remotely locatable cryocooler system. Likewise, the high voltage source needed to operate the crystal is remotely locatable and flexibly connected to the crystal. The sensing probe which contains the excitation source, the crystal detector, a pulse amplifier and the cryostat (for cooling the crystal) is the instrument used for exciting and detecting the X-radiation spectrum. The sensing probe is miniaturized, portable, and suitable for reaching remote places.

In broad terms, the system permits fast non-destructive analysis of solids, powder, slurries or liquids on a qualitative or quantitative basis and is able to detect all elements from sodium to uranium. The system has been conceived for specific applications such as steam generator performance evaluation and power plant component analysis. It is designed to provide services where the analytical data must necessarily be obtained in situ because of size, weight or location of the object of interest or because of a need for immediate results. The system permits field analysis utilizing streamlined analytical procedures which presently require complex sampling by in situ sorting and screening. The entire system is flexibly connected, easily dismantled and reassembled, thus being suitable for immediate relocation.

BRIEF DESCRIPTION OF THE DRAWINGS

FIG. 2 is a pictorial diagram of the system and its interconnected component parts.

DESCRIPTION OF THE PREFERRED EMBODIMENT

Figure 1:
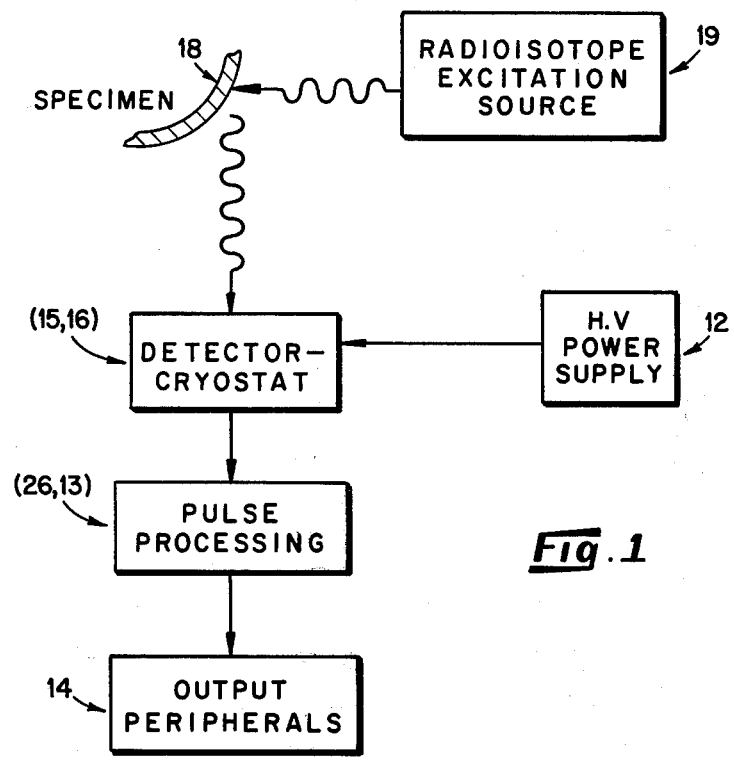
FIG. 1 is a schematic diagram of a radioisotope excited X-ray multichannel analyzer system representative of the present invention.
Figure 3:
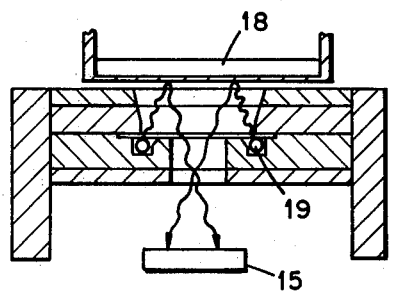
FIG. 3 depicts an irradiator with an excitation source.

Referring to FIG. 2, it can be seen that the present system comprises of four major component units; a helium compressor 10, a sensing probe 17, a high voltage power supply 12, and a multichannel pulse analyzer 13. The purpose of the compressor or crycooler is to provide a cryogenic station for the solid state detector 15. This is achieved by circulating compressed gas, such as helium, through a cryostat which is appropriately located with respect to the detector. Suitable cryostats and cryocoolers are commercially available. A typically useful unit consumes 1000 watts of single phase 110 voltage power, which is generally available in most locations, weighs approximately 85 pounds. Its dimensions are 13 by 20 by 13 inches.

The unit provides cryocooling on demand. Commercially available cryocoolers can run continuously without logistic support or operator attendance. They fail-safe in the event of power loss or overload and require only about twenty minutes of maintenance every several thousand hours of operation. The reliability of cryocoolers has been demonstrated by the performance of compact units installed in aircraft for use with airborne sensing devices.

In all commercially available energy dispersive X-ray analyzers the cryogenic requirements of the detector are satisfied by liquid nitrogen coolant which requires a draw reservoir to be filled periodically with liquid nitrogen, adding to the weight and total bulk of the system, and restricting the handling and freedom of positioning of the probe.

As a result of the compact configuration of the sensing probe 17 shown in FIG. 2, specimens in remote locations can be reached and the fluoresced characteristic X-radiation spectrum emitted from the specimen can be detected. As shown in FIG. 2 cylindrical probe 17 comprises an irradiator 25, provided with a shielded recess 20 for holding the radioisotope source 19, an X-radiation detector 15 such as a Lithium drifted silicon detector, located in heat exchange relationship with cryostat 16, a pulse preamplifier 26 for amplifying the X-radiation Signals and connector receptable 23 and 24.

Radiation sources are available in a wide variety of shapes and configurations. For example, the source shown is in the configuration of a disc and is commercially available. Examples of radioactive elements which may be used include $^{55}$Fe, $^{109}$Cd and $^{241}$Am, all of which are well-known in the art and are commercially available. The Kevex Application Guide is a publication that those skilled in the art might consult for guidance in selecting the proper sources.

The probe used in the present system has been compacted into a structure 2.75 inches in diameter and approximately 11 inches in length. This design is based on commercially available parts. The configuration of the probe has been made possible by the elimination of the draw reservoir for liquid nitrogen, which is an integral part of the detector in all existing instruments. In addition, the electronics for the preamplifier and all connectors and terminals have been located in the back of the probe, and protruding detector housing flanges have been eliminated. The overall design makes it possible to have the probe pass through ports as small as 3 inches in diameter to reach regions of difficult access for analysis. The helium and electric lines connecting the probe are completely flexible.

The cryogenic fluid circulates through the analytical head under the control of a gas compressor. The arrangement provides for easily handling and maneuvering the probe which can be operated in any orientation and at any place or position. The restrictions inherent in liquid nitrogen cryostats are completely eliminated as was observed with respect to FIG. 2. The probe is connected to the multichannel analyzer 13, the power supply 12, and to the cryocooler 10 by flexible cables 27A and 27B and tubing 14A and 14B.

The multichannel pulse analyzer as shown in FIG. 2 is for the purpose of receiving, sorting, storing and counting X-radiation signals received from the pulse amplifier that is located in the sensing probe. The analytical results may be displayed by oscilloscope or recorded by an X-Y plotter. Suitable units are commercially available. A A typical unit is 11 inches wide, 14 inches long and 10 inches high and weighs approximately 18 pounds. It requires an electrical power source of 1.5 KW at 115 volts AC, 60 Hz, single phase.

The high voltage power supply 12 shown in FIG. 2 provides the operating high voltage, in the order of 750 volts, required for the proper operation of the solid state crystal detector. Suitable units varying in size and weight are commercially available. The operating voltage will vary somewhat depending on size and type of solid state crystal detector used. Most high voltage power units are equipped with means of adjusting the output voltage to a desired level over a wide range of operating voltages.

Referring again to FIG. 2, it is noted that the flexible tubular gas lines 14A and 14B, providing the closed cycle conduit for the compressor, and flexible connectors 27A and 27B are of a kind that are commonly associated with the use of the respective units. Their operative characteristics are not critical. Special insulation is not required and they are commercially available.

Cryostat 16 located in sensing probe 17 is in heat exchange relationship with the crystal detector 15. High voltage power supply 12 is electrically connected by flexible cable 27B to the crystal detector 15, which is connected to the multichannel (chemical) analyzer 13 through pulse preamplifier 26. Flexible tubular cables 14A and 14B and flexible connector cables 27A and 27B are combined in a single harness 11 for compactness and streamlining of the system. There is literally no restriction on the length of harness 11 thereby permitting probe 17 to be extended long distances from the other component parts.

Referring again to FIG. 2, connector receptacles 23 and 24 facilitate the connection of the gas line cables and connector cables from the harness to the probe. The irradiator face 25 directs the radiation of the radioisotope fluorescent source 19 to the specimen 18 and allows the X-ray radiation spectrum returning from the specimen 18 to intersect the detector 15 which is mounted on the platform of the cylindrical cryostat 16. The output from the crystal detector 15 is received by the pulse preamplifier 26 which is internally connected to receptacle connector 23. The analytical process utilized in this system is similar to those in current use in that the radioisotope 19 excitation source is used to fluoresce the characteristic X-radiation of the elements present in the specimen sample 18. The solid state detector crystal 15 is utilized to measure with very high resolution the energies of the X-ray photons generated by the specimen sample 18. The output pulse amplitude of the detector is directly proportional to the energy of each incident S-ray photon absorbed by the crystal. This energy allows the identification of the emitting element. The pulses are relayed to the pulse preamplifier 26 where they are amplified and transmitted to the multichannel X-ray analyzer for sorting and displaying. In this respect the present system resembles conventional commercially available systems. However, as has already been pointed out it is the flexibility, portability and self-supporting capabilities of the system which is the essence of the present invention.

In addition to its usefulness in the field, the proposed system can also be advantageously utilized as an X-ray analyzer in the laboratory, and characteristics of this system will provide an added capacity in some laboratory situations. Because of its freedom in positioning, the sensing head can be placed vertically directly above liquids or powder samples requiring analysis. As a result these materials can be excited and analyzed without the interference or absorption caused by a container or holder. This ability is important when light elements are involved in the analysis where even thin film holders can introduce a significant absorption of the soft radiation emitted by the light elements.

The portability of the system has not detracted from its sensitivity as an X-ray chemical analyzer which is equivalent to that of the energy dispersive spectrometers (EDS). EDS sensitivity depends on the analyses procedure. Solutions can be analyzed directly, or the elements of interest can be concentrated by precipitation or ion exchange processes. X-ray integration times are normally established on the basis of data precision requirements. A value of $1 \times 10^{-6}$ grams per cm$^3$ is a typical level of sensitivity for EDA procedures.

Referring again to FIG. 2, these units and their respective interconnecting cables and tubing constitute and easily transportable set. The unit can be interconnected and made ready for operation in less than one hour.

While the present invention has been displayed and discussed with respect to the preferred embodiments it is obvious that other configurations could be used.

What is claimed is:

1. A self-contained portable field X-ray multichannel analyzer for in situ analysis of the chemical composition of a specimen comprising:
   a cylindrical sensing probe having
      means for receiving electrical energy and a cooling fluid at one end thereof, and an irradiator head at the other end thereof, said irradiator head containing

- a radioactive γ emitter adapted to irradiate said specimen with γ-rays, thereby generating X-ray photons having an energy spectrum chacteristic of the chemical composition of said specimen;
- a radiation detector adapted to receive said X-rays and produce output electrical pulses having an amplitude proportional to the energy level of said X-ray photons;
- a pulse amplifier connected to said detector adapted to receive said output pulse and provide an amplified output pulse thereof; and
- a cryostat in a heat exchange relationship with said detector so as to maintain said detector at a cryogenic temperature;

a closed cycle cryocooler, said cryocooler being remotely locatable with respect to said cryostat, flexibly coupled thereto and adapted to provide a closed cycle circulation of compressed coolant through said cryostat so as to maintain said detector at a cryogenic temperature, independent of any supply of consumable cryogenic fluid;

a multichannel X-ray analyzer adapted to receive, sort, store, count and record said X-ray photons present in said X-radiation energy spectrum, said multichannel X-ray analyzer being remotely locatable with respect to said pulse amplifier and flexibly electrically connected thereto so as to receive said output pulse therefrom;

a voltage source adapted to provide an operating voltage potential for said energy dispersive spectrometry detecting means; and means for connecting said operating voltage potential across said detecting means, said connecting means being flexible so as to facilitate remote relocation of said voltage source with respect to said detecting means.

2. The apparatus described in claim 1 wherein said radiation, detector is a Lithium drifted silicon detector.

3. The apparatus described in claim 1 wherein said coolant is compressed helium gas.

* * * * *